United States Patent [19]

Blankenship et al.

[11] Patent Number: 4,666,582
[45] Date of Patent: May 19, 1987

[54] COOLANT CONDITION SENSOR APPARATUS

[75] Inventors: Gene E. Blankenship, Richardson, Tex.; Edward M. Gonsalves, Swansea; Keith W. Kawate, Attleboro Falls, both of Mass.; Stephen P. Sacarisen, Richardson, Tex.; William H. Giolma, Dallas, Tex.; Damir A. Spanjol, Richardson, Tex.

[73] Assignee: Texas Instruments Incorporated, Dallas, Tex.

[21] Appl. No.: 780,467

[22] Filed: Sep. 26, 1985

[51] Int. Cl.⁴ ............................................. G01N 27/26
[52] U.S. Cl. ....................................... 204/404; 340/59
[58] Field of Search ........................... 73/118, 432 B; 123/41.15; 204/1 T, 404; 324/435, 436; 340/59

[56] References Cited

U.S. PATENT DOCUMENTS

| | | | |
|---|---|---|---|
| 3,416,131 | 12/1968 | MacKenzie et al. | 340/59 |
| 3,717,566 | 2/1973 | Wilson | 204/404 |
| 3,855,101 | 12/1974 | Wilson | 204/404 |
| 3,939,470 | 2/1976 | Arai et al. | 123/41.15 |
| 4,147,596 | 4/1979 | Baboian et al. | 123/41.15 |
| 4,253,064 | 2/1981 | McBride, Jr. | 324/436 |
| 4,575,678 | 3/1986 | Hladky | 204/404 |

Primary Examiner—Jerry W. Myracle
Assistant Examiner—Robert R. Raevis
Attorney, Agent, or Firm—John A. Haug; James P. McAndrews; Melvin Sharp

[57] ABSTRACT

A dual function sensor particularly useful with vehicular coolant systems indicates when a coolant liquid becomes corrosive to such cooling system materials as well as when the liquid falls to a low level condition. A reference and a sense electrode are used to probe the condition of the coolant liquid. Integral electronics provide signal conditioning and transmitting to indicate both corrosive and low level coolant conditions. The sensor assembly mounts directly onto a tubular coupling on the vehicle radiator by pushing the assembly onto the coupling until a spring wire element snaps past a lip formed on the free distal end of the coupling. An electrical connector shroud extends from the assembly and accommodates a mating male connector which is pushed onto the shroud until a clip mounted on the male connector snaps over a locking tab located on the shroud. The male connector typically is connected to an engine control module (ECM).

21 Claims, 12 Drawing Figures

COOLANT CONDITION SENSOR APPARATUS

CROSS REFERENCES TO RELATED APPLICATIONS

Application Ser. No. 780,468, filed of even date herewith contains related subject matter to that of this application.

BACKGROUND OF THE INVENTION

1. Field of the Invention

This invention relates generally to apparatus for monitoring selected conditions of liquid, such as engine coolant in a vehicular radiator, and more particularly to a sensor which can be used to provide remote indication of the degree of corrosivity of the coolant, the presence or absence of the coolant at a selected level in the radiator or both conditions as desired.

2. Description of the Prior Art

Vehicular cooling systems are composed of several components which include the radiator, circulating pump, passages in the engine block and associated tubing. Since the system is composed of metallic parts, there is a need to prevent, or at least mitigate, corrosion in order to prolong the useful life of the system. To this end it has become common practice to add chemical substances to the coolant liquid which serve to inhibit corrosion of the metal surfaces which come in contact with the liquid. Such substances are known as inhibitors and generally form a film on the metal surfaces thereby protecting them from corrosion. Thus, commercially available permanent antifreeze includes an inhibitor which is effective in preventing corrosion, however, over the course of time the corrosion inhibiting characteristic of the liquid can become less effective due to various factors.

At the present time the use of aluminum for cylinder heads and cooling systems in automobiles is becoming more common. Aluminum cylinder heads run hotter than iron cylinder heads. This combined with aluminum's higher susceptibility to corrosion leads to the potential for a phenomena known as "hot transport corrosion." This is a process whereby aluminum corrosion products are transported from the hottest areas, typically in the head, to the coolest, that is, the radiator. These contaminants interfere with good heat transfer and degrade the heat rejection capability of the system. Aluminum heads are also less tolerant to overheat conditions than iron and run the risk of warping at elevated temperatures which can result from a low coolant condition. Also, the aluminum used in radiators and heater cores is more susceptible to corrosion than the traditional copper-brass system which makes proper maintenance more critical to prevent failure due to perforation.

In U.S. Pat. No. 4,147,596, assigned to the assignee of the present invention, a system is disclosed and claimed in which a potential measuring circuit employing at least two electrochemical electrodes composed of dissimilar metals is located so as to be immersed and in contact with coolant liquid. The electrodes are mounted in a tubular housing which is provided with a threaded portion so that it can be screwed into a threaded bore of a wall confining the coolant liquid. When the inhibiting characteristic is effective, a first range of electrical potential exists between the electrodes; however, when the inhibiting characteristic becomes ineffective for any reason, a second range of electrical potential exists therebetween. Upon reaching a threshold level, as the potential moves into the second range, indicating means are actuated to provide a suitable indication of the condition.

In U.S. Pat. No. 4,253,064, also assigned to the assignee of the present invention, another condition of the coolant is sensed utilizing the same electrodes which are part of a coolant inhibition characteristic condition sensing system. In that system the presence or absence of liquid is determined by making use of the electrical resistance between the two electrodes without causing any appreciable current through the liquid which current would adversely effect the ability to sense the coolant inhibition characteristic condition. The resistance between the electrodes serves as part of a feedback network in a feedback oscillator. The feedback oscillator incorporates a dc measuring amplifier for measuring the electrode potential as an indication of the corrosion inhibition characteristic of liquid in which the electrodes are immersed. The same amplifier provides the amplification necessary for oscillation when the resistance between the electrodes increases to a threshold level indicating an absence of liquid. The feedback network includes a capacitor which not only determines the frequency of oscillation, along with appropriate resistance, but also blocks any possible DC current which might otherwise flow through the electrodes. The sensing of liquid presence or absence is accomplished between a first electrode and ground while the second electrode may be directly grounded, coupled to ground through a large capacitor or resistor or separated from the first electrode by an electrically insulative barrier and thus coupled to ground through the liquid clinging to the insulator separating the second electrode from ground.

However the use of the feedback network in both the coolant inhibition characteristic sensing function and the level sensing function tends to limit the flexibility of the system. For example, adjusting the threshold sensing parameters of one function sometimes may affect the other function. The use of the feedback network in both functions also subjects the system to some degree of noise sensitivity which could cause nuisance tripping under certain conditions. Another limitation of the prior art involves the fact that the electrochemical sensing of corrosivity requires the sensing of negative potentials. In dealing with this the prior art provided a negative power supply which rendered the system more complex and costlier than desirable. Another limitation was the output format of the system (DC output for corrosivity and AC output for low level). This made sensor output difficult to decode.

It is an object of this invention to sense electro-chemical potentials of electrodes in a liquid, including potentials below ground, as an indication of corrosivity of the liquid as well as sensing the presence or absence of the liquid using a common set of electrodes. Another object is the provision of a system which can be used to sense either the function of corrosion inhibition effectiveness of a liquid or the function of the presence or absence of such liquid or both functions if desired. Yet another object is the provision of a sensor used for either or both functions which is readily mounted on a vehicular cooling system which is inexpensive yet reliable and long lasting. Another object is the provision of a sensing system for sensing the functions of liquid corrosivity and liquid level for which the threshold values for the function are readily and independently calibratable and one which has selected hysteresis which is also calibratable. It is another object of theinvention to provide an engine coolant condition sensor assembly which is inexpensive to manufacture and is easily installed in a liquid reservoir in a tamper proof manner. Another object is the provision of such a sensor assembly which houses not only the sensing elements but also electronics used to process or condition the electrical signal generated by the sensing elements and transmit it to a remote location, such as the instrument panel of an automobile, to give visual or audio indication of the condition of the coolant.

Other objects, advantages and details of the apparatus provided by the invention appear in the following detailed description of the preferred embodiment of the invention.

Figure 1:
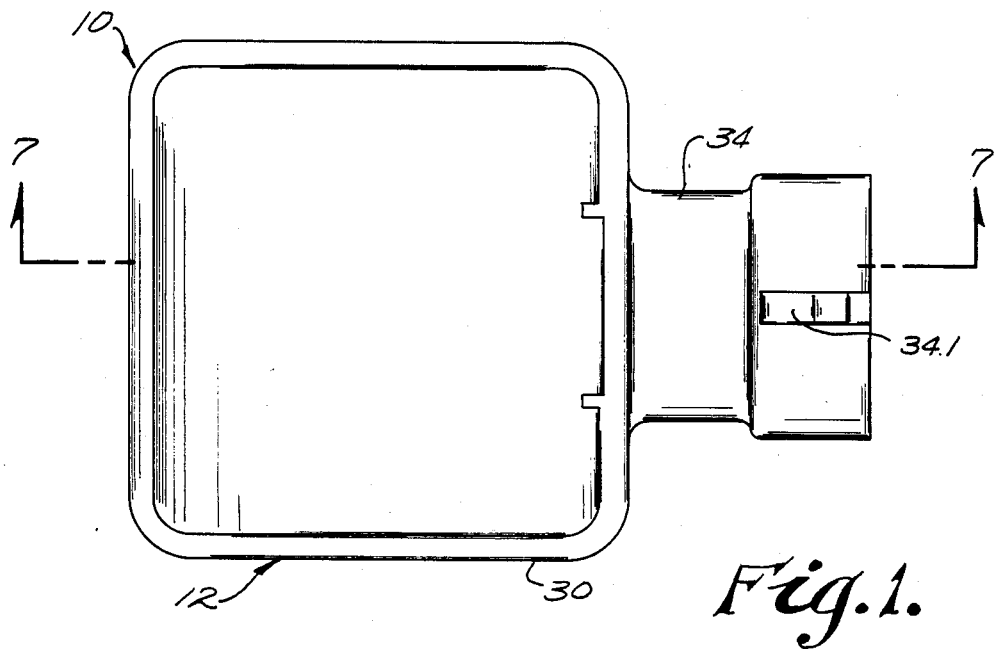
FIG. 1 is a top plane view of a sensor assembly made in accordance with the invention.
Figure 2:
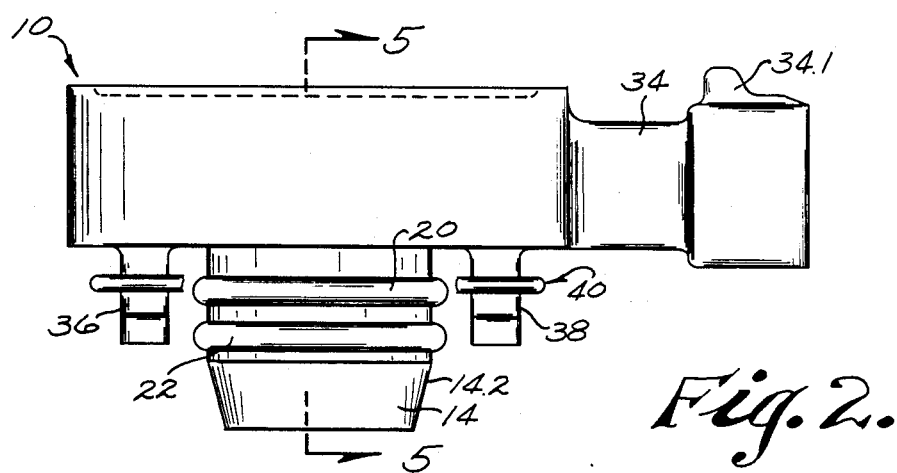
FIG. 2 is a front elevation of the FIG. 1 assembly.
Figure 3:
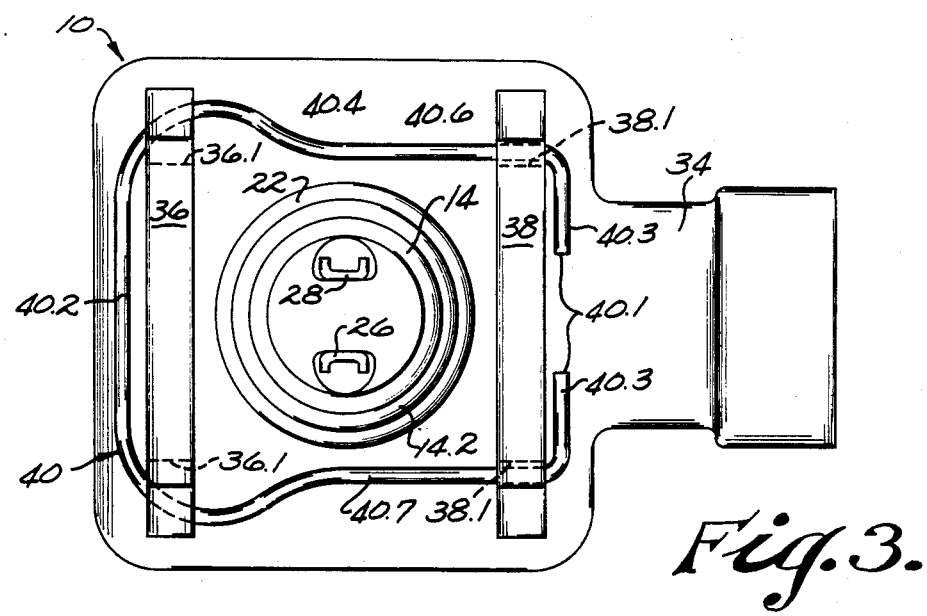
FIG. 3 is a bottom view of the FIG. 1 assembly.
Figure 4:
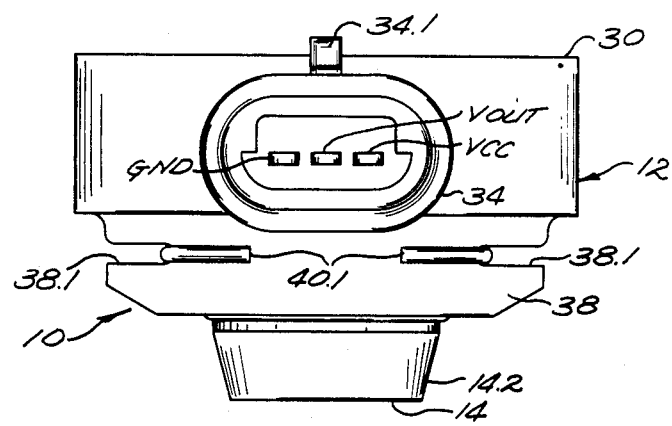
FIG. 4 is an side view of the FIG. 1 assembly.

Dimensions of the parts shown in the drawings may have been modified for purposes of clarity of illustration.

SUMMARY OF THE INVENTION

Briefly, in accordance with the invention a sensor assembly housing has a first generally tubular compartment open at one end which is adapted to be telescopically received in a tubular coupling of a vehicular radiator. A pair of spaced "O" rings provide a liquid tight seal between the tubular compartment and the coupling. First and second electrodes, elongated elements each having a generally U-shaped configuration in cross section taken perpendicular to its longitudinal axis, are disposed in the tubular compartment with a fixed end attached to a rivet which extends through an "O" ring seal into a generally parallelepiped configured second compartment. The second compartment contains a circuit board mounting electronics used to condition the electrical signals received by the electrodes and transmit them to a remote location such as an engine control module and the dashboard of the vehicle. The electronics are potted in the second compartment to provide an effective environmental seal. A connector shroud extends from one side of the second compartment to permit attachment to an appropriate wire harness.

According to a feature of the invention, the housing has side wall means formed with grooves adapted to receive a spring wire locking element. The locking element has first opposed portions adapted to be received in the grooves and second opposed portions which are adapted to be received under a lip formed on the outer distal end of a tubular coupling of the radiator. In mounting the sensor assembly to a radiator, the spring locking element is placed with the first opposed portions received in the grooves of the housing walls. The second opposed portions of the wire project inwardly so that at their at rest position they are spaced from one another a distance which is less than the outer diameter of the tubular coupling. The housing is merely pushed onto the tubular coupling with the second opposed portions being cammed away from each other until the outer lip is passed at which point the second opposed portions of the wire spring back toward each other under the lip to securely lock the housing onto the coupling. In order to remove the housing the free ends of the wire are pried apart to move the second opposed portions of the wire away from each other a distance greater than the outer diameter of the lip.

According to another feature of the invention the electronics comprise two integrated circuits, the first containing two PMOS devices which allow sensing of negative potentials and also provide isolation between the electrodes and between the electrodes and ground. These devices shift a negative potential to a positive potential which is outputted to a bipolar integrated circuit.

According to a feature of the invention the operation threshold for corrosion inhibition sensing is adjustable by changing either a current reference resistor or a bias resistor which are separately connectable to the bipolar integrated circuit. The hysteresis of the corrosivity sensing is adjustable by connecting a resistor between two designated pins of the bipolar integrated circuit.

According to yet another feature of the invention the level sensing portion uses the impedance between the two electrodes and is adjustable over a wide range of resistance threshold by varying a resistor-capacitor leg that connects to the bipolar integrated circuit. A capacitor is used as a noise filter to improve the switching characteristics of the sensor while two diodes are used to provide a 1.4 volt band of hysteresis.

According to a feature of the invention the output of the low level and corrosive circuits contained within the bipolar integrated circuit are combined into a logic network that results in a low level indication overriding a corrosivity warning.

DETAILED DESCRIPTION OF THE PREFERRED EMBODIMENT

Figure 5:
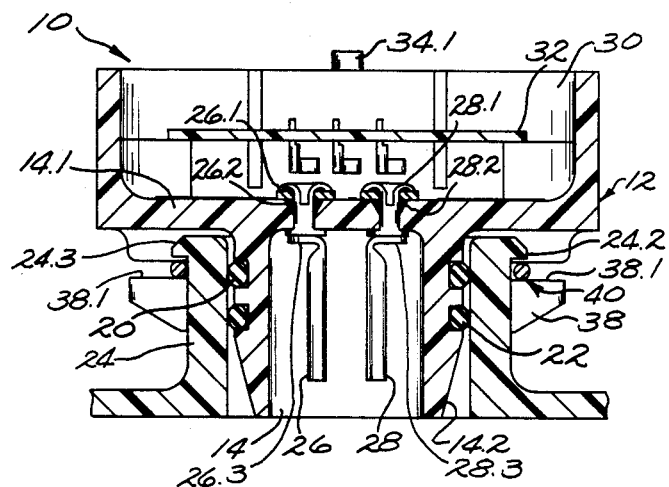
FIG. 5 is a cross sectional view taken on line 5—5 of FIG. 2 with the addition of a tubular coupling of an automotive radiator on which the sensor assembly is mounted and with the circuit components on circuit board 32 and the encasing potting material not shown.
Figures 6, 6A:
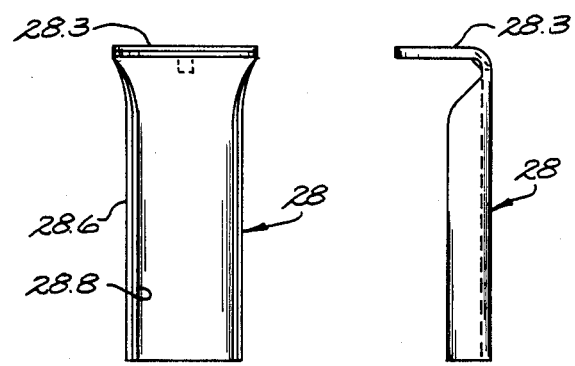
FIGS. 6 and 6a are enlarged elevation view, front and side respectively, of a bimetal sense electrode.
Figure 7:
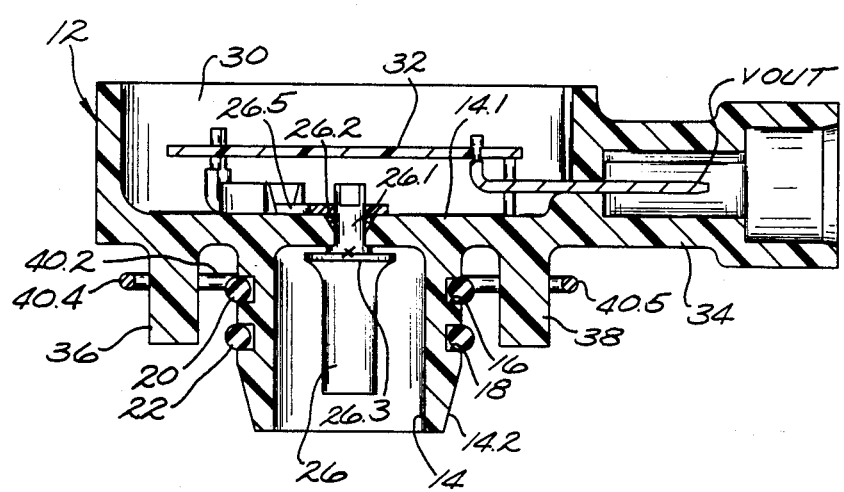
FIG. 7 is an enlarged view in cross section of a sensor assembly taken on line 7—7 of FIG. 1 with the circuit components on circuit board 32 and the encasing potting material not shown.

Referring now to the drawings numeral 10 indicates a sensor assembly made in accordance with the invention. Assembly 10 includes a housing 12 preferably molded of suitable electrically insulative material such as Zytel, a trademark of E. I. duPont de Nemours & Co. for glass filled nylon, having a first generally tubular compartment 14. The side wall of tubular compartment 14 is provided with two circular grooves 16, 18 spaced from one another along the longitudinal axis of the tubular compartment. "O" rings 20, 22 are disposed in the respective grooves to provide a fluid tight seal between the compartment 14 and a tubular coupling 24, shown in FIG. 5, in which the compartment is received.

With particular reference to FIGS. 3 and 5-7, first and second electrodes 26, 28 are disposed within compartment 14, each having a base plate 26.3, 28.3, welded to a rivet, 26.1 and 28.1 respectively, which extends through a respective aperture in wall member 14.1 for connection with electronics to be described below. "O" rings 26.2 and 28.2 are received around the rivets and are disposed in grooves formed in wall member 14.1 in communication with the respective apertures to provide a fluid tight seal. Suitable connectors, such as connector 26.5 interconnect the rivets with the electronics as well as capture "O" rings 26.2, 28.2 in their respective grooves.

The outer portion of tubular compartment 14 is preferably formed with a taper 14.2 to facilitate the placement of the compartment into tubular coupling 24.

Housing 12 has a second compartment 30, generally configured as a parallelepiped, to accommodate electronics used to condition the signals received from the electrodes and transmit the conditioned signals to a remote location such as the dashboard of a vehicle. The electronics are mounted on a circuit board 32 as will be described infra and are potted therein by any suitable electrically insulative potting material to provide an effective environmental seal.

A connector shroud 34 extends laterally from one of the side walls of compartment 30 and encloses spaced terminals GND, VOUT and VCC which extend through the wall of the compartment from circuit board 32. A suitable wiring harness (not shown) is receivable in the shroud for connection to the thermal. Preferably a locking tab 34.1 is provided on shroud 34 to lock the harness in its position of connection with the terminals.

Electrode 26 is a reference electrode and is preferably formed of silver but could also be formed of other standard commercial reference material such as the calomel family, silver alloys including Ag/Ag halide and Ag/AgO, the copper family such as Cu/Cu halide and Cu/CuSO$_4$ or other stable reference material.

Electrode 28 is a sense electrode and is preferably formed of a clad element having a first layer 28.6 of steel bonded to a second layer 28.8 of aluminum. These materials are especially adapted for use with cooling systems which embody aluminum components, as taught in U.S. Pat. No. 4,147,596 mentioned supra. If the sensing system of the present invention is used in other environments, then other sense electrode materials could be used depending on the materials used for the components to be monitored.

Electrodes 26, 28 are elongated elements extending in a direction generally parallel to the longitudinal axis of the tubular compartment 14 and are formed with a base plate 26.3, 28.3 bent at an angle of approximately 90° to the remainder of the electrode. The base plate is welded or otherwise suitably fixed and electrically connected to a rivet as described above. The remainder of the length of the electrode is generally U-shaped with respect to a cross section taken perpendicular to the longitudinal axis of compartment 14, the side walls of the U-shape providing mechanical strength to the electrode.

Housing 12 is also provided with opposed side wall members 36, 38 depending downwardly from wall 14.1 with grooves 36.1, 38.1 formed at opposite ends of each wall member. A spring wire locking element 40 is received in grooves 36.1, 38.1 and is used to lock the assembly to a coupling member such as the tubular coupling 24 of a vehicular radiator. Element 40, best seen in FIG. 3, may be formed of a length of stainless steel or other suitable wire material and is bent into a generally rectangular configuration with opposite ends 40.1 spaced slightly apart in the middle of one of the legs of the rectangle. Opposed legs 40.2 and 40.3 are generally straight while opposed legs 40.4 and 40.5 are bent inwardly so that opposed portions 40.6 and 40.7 in respective legs 40.4 and 40.5 are at a distance from one another which is less than the outer diameter of an outwardly extending lip 24.2 formed on the free distal end of tubular coupling 24 (see FIG. 5).

The assembly 10 is normally provided to the vehicle manufacturer with lock element 40 already disposed in grooves 36.1, 38.1 so that all that need be done in installing the assembly is to push it onto tubular coupling 24. As the coupling engages the spring element 40, it pushes portions 40.6 and 40.7 further apart until element 40 passes beyond the lip at which point the portions 40.6 and 40.7 spring back toward one another and against the outer wall of tubular coupling 24 below lip 24.2. In this regard, it is preferred that lip 24.2 be formed with a taper 24.3 (FIG. 5) to facilitate the outward camming action of portion 40.6 and 40.7 as the assembly is installed.

With the assembly mounted in its locked position, there is no danger of it becoming accidentally dislodged or loose, as would be the case if a conventional threaded connection were used. Further, the need for protecting threads of a conventional connection from damage prior to installation is obviated and the time required for installation substantially reduced compared to connection techniques using threaded members.

If it is desired to remove the assembly, ends 40.1 are pushed apart until portions 40.6 and 40.7 are spaced from one another a distance greater than the diameter of lip 24.2 at which point the assembly can be slipped off the coupling.

Figure 8:
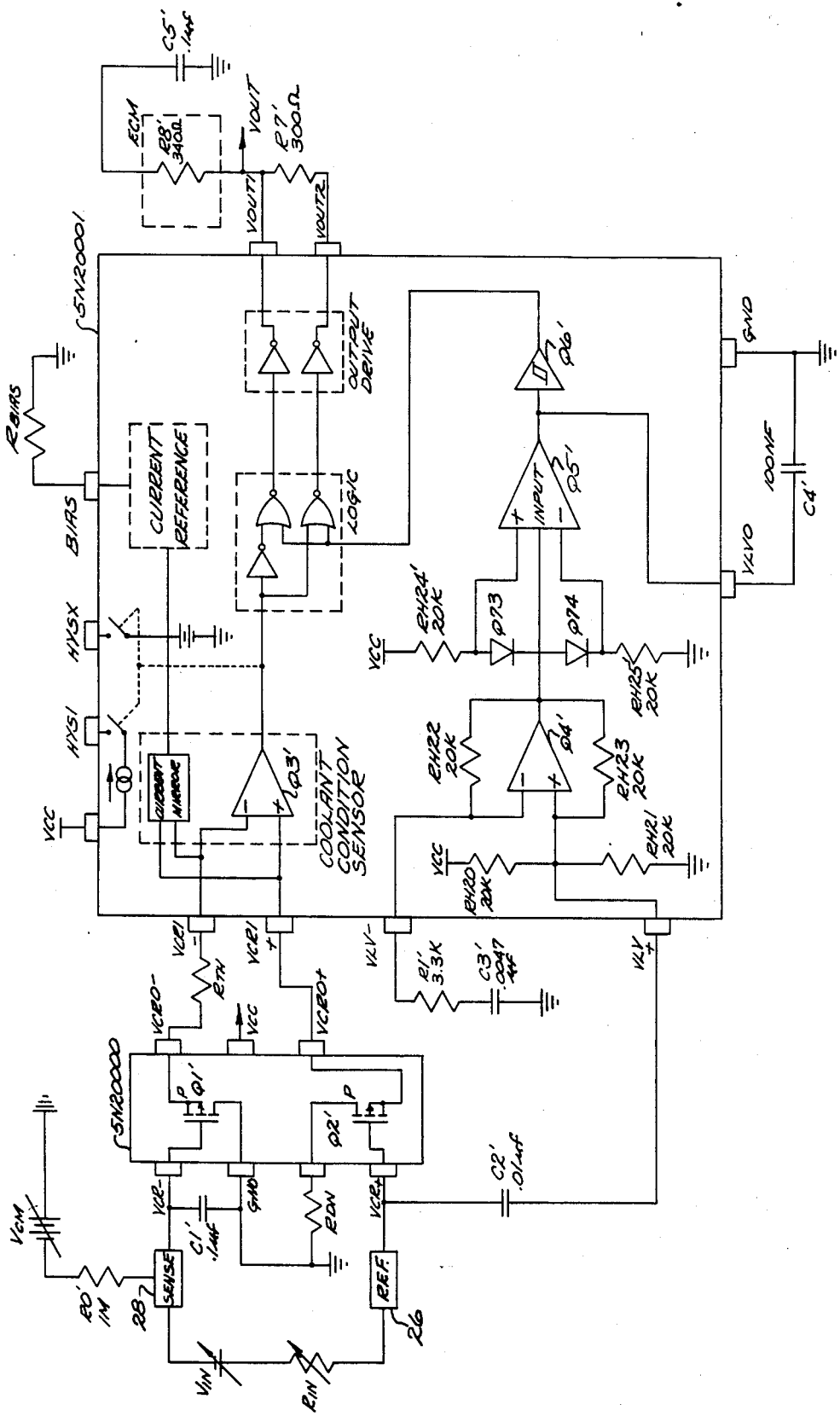
FIG. 8 is a block diagram of custom integrated circuits used in the sensor assembly to process and transmit the electrical signals generated by the electrodes.
Figure 9:
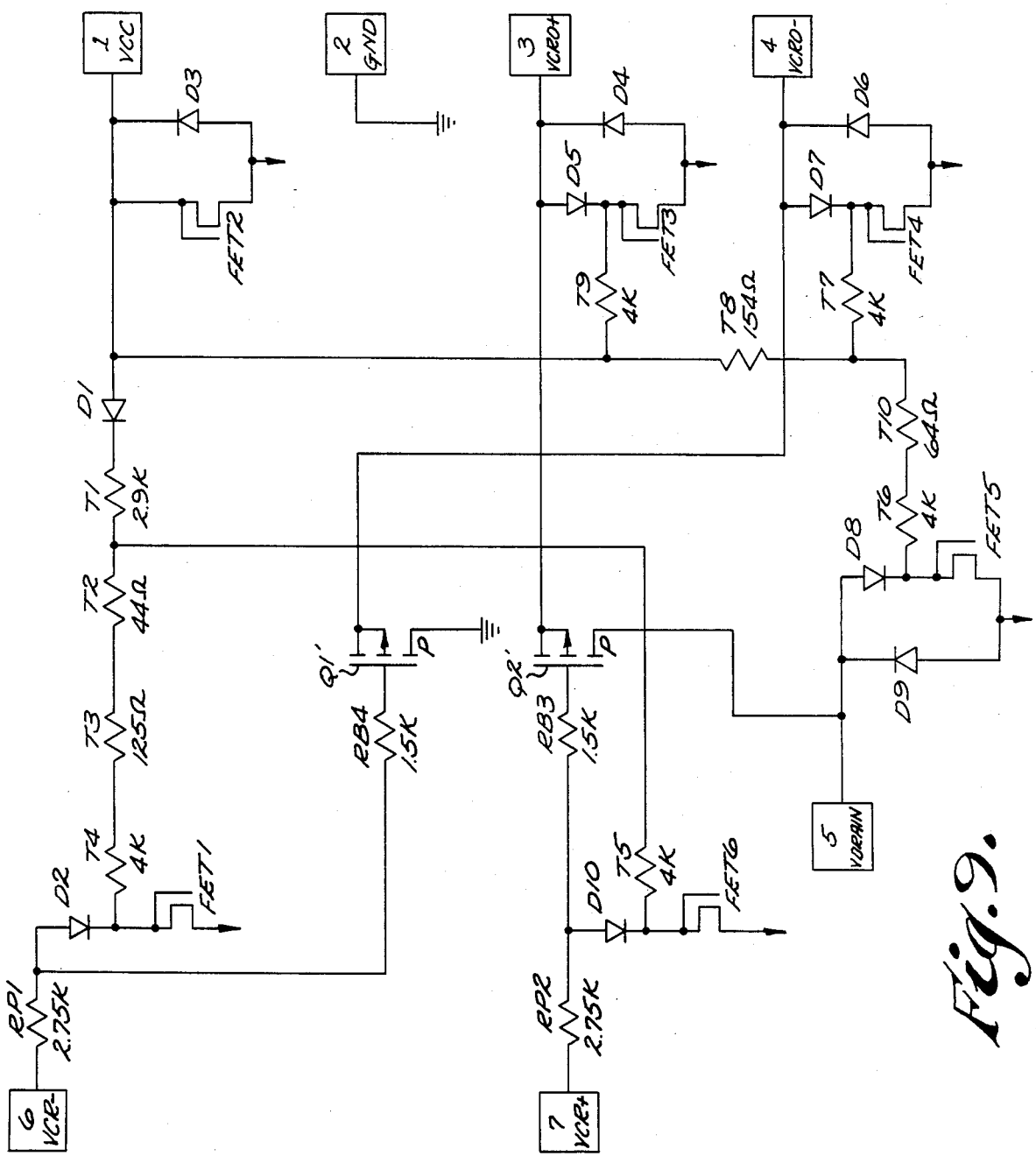
FIG. 9 is a schematic diagram showing a potential level shifting portion of the input/conditioner integrated circuit of FIG. 8.
Figure 10:
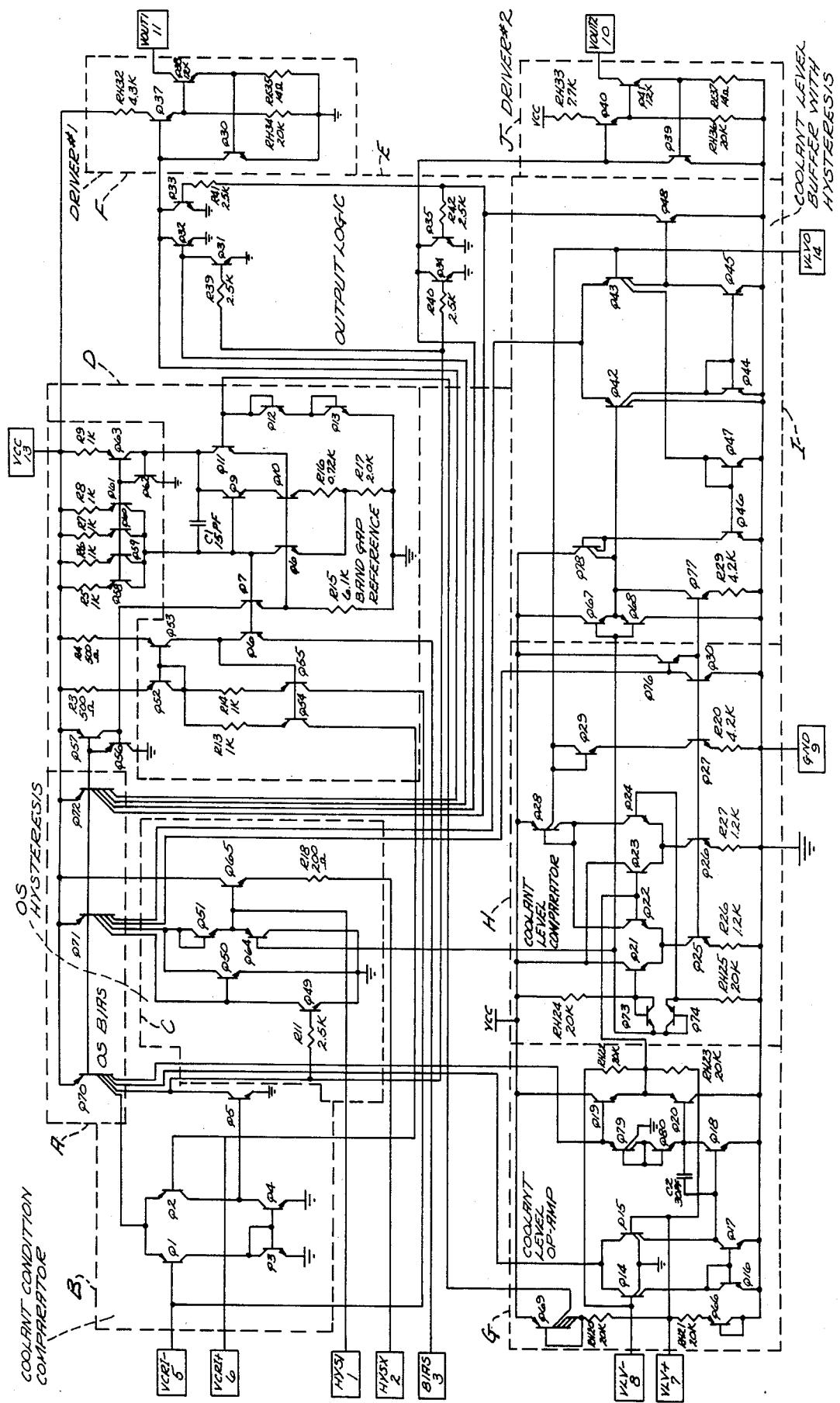
FIG. 10 is a schematic diagram showing the processing integrated circuit.

The circuitry used in practicing the invention will be described with particular reference to FIG. 8 showing a block diagram of the electronic components mounted on circuit board 32 and FIGS. 9 and 10 showing schematically such circuitry. The circuit utilizes two surface mounted, custom integrated circuits, the first a CMOS chip SN 28880 (referred to below as '80) and the second a bipolar chip SN 28881 (referred to below as '81). As seen in FIG. 8 $V_{IN}$ and $R_{IN}$ represent the coolant liquid in which electrodes 26 and 28 are immersed. As the corrosion inhibition characteristic of the fluid varies, the potential difference generated between the two varies. The $R_{IN}$ varies based on whether the electrodes are immersed or not, that is, when inundated there may be, by way of example, an $R_{IN}$ resistance on the order of one hundred ohms but when the level of the coolant falls below the electrodes exposing them the $R_{IN}$ increases beyond ten thousand ohms.

RO' is a one megohm resistor connected between electrode 28 and $V_{CM}$ (V common mode) which is in turn shown connected to ground. $V_{CM}$ and RO' comprise a representation of the electrode potentials and resistances with respect to engine ground.

The '80 device is constructed using CMOS technology in order to provide low input leakage, high input impedance to obviate the possibility of electrode loading as well as to allow sensing of potentials a volt below the negative supply rail, which in the present case, is ground, and comprises PMOS transistors Q1' and Q2'. The input from electrode 28 through pin VCR− of the '80 device is connected to the gate of Q1' and the input from electrode 26 through pin VCR+ is connected to the gate of Q2'.

Each input of the '80 integrated circuit is preferably provided with electrostatic discharge (ESD) protection comprising diodes D2-D10—fixed effect transistors FET 1-FET 6 network to protect the circuit components from both positive and negative voltage spikes. As seen in FIG. 9, networks comprising devices D1-D10, RP 1, 2 and T1-T10 provide ESD protection and bias to the circuit inputs of the '80 circuit and insure very low current leakage into the electrode probe inputs at elevated temperatures. Leakage greater than 100 nano amperes over an extended period of time would degrade the electrochemical potential developed by the electrodes.

Transistors Q1' and Q2' level shift the potentials of the circuit inputs VCR− and VCR+ from the electrodes from a low as much as one volt below ground up to a level above ground with their outputs taken from the FET sources and supplied to VCRO− and VCRO+ pins which are connected to the '81 integrated circuit.

Thus the '80 IC allows the '81 bipolar IC to see potentials within its common mode range (above ground) while providing little or no input leakage current which would adversely effect sensor potentials.

Turning back to FIG. 8, resistor $R_{TH}$ connected between pin VCRO− of the '80 device and VCRI− of the '81 device sets the threshold at which the system works as will be referred to in more detail below. In order to negate the offset error introduced by the use of resistor $R_{TH}$ causing different current flow between the two transistors Q1' and Q2', resistor $R_{DN}$ (drain) is connected between the drain of transistor Q2' and ground to balance the current flow through the transistors.

Capacitor C1' coupled between pin VCR− and ground is an AC decoupling capacitor which allows use of the same electrodes for sensing of both level and corrosion inhibition. Capacitor C2' connected between electrode 26 and pin VLV+ of the '81 device is also part of the decoupling network.

Pin VCRO− of the '80 device is connected to pin VCRI− of the '81 device through resistor $R_{TH}$ while pin VCRO+ is connected directly to pin VCRI+ of the '81 device. As mentioned above, the potentials seen at pins VCRI− and VCRI+ are shifted up from the potentials seen at the electrodes so that both potentials are positive.

Resistor R1' is serially connected to capacitor C3' and both are connected between pin VLV− of the '81 device and ground. Changing the values of these components will change the threshold value of the level sensing function as will be described in more detail below.

A resistor $R_{BIAS}$ is connected between pin BIAS of the '81 device and ground. This resistor determines the amount of current which passes through resistor $R_{TH}$. A change in the value of resistor $R_{BIAS}$ will therefore change the current reference. The current reference also provides positive hysteresis. For example, if the device were triggered at 300 mv, it would not turn off until a selected lower value is reached, for example 200 mv. In the preferred embodiment the device is initially set at a hysteresis value of 100 mv by connecting the HYSI pin to the BIAS pin. This value can be changed by connecting a resistor (not shown) between the HYSX pin and the BIAS pin. These options are schematically shown by the switches connected to pin HYSI and HYSX and interconnected by dotted lines on FIG. 8.

The dashed line block labeled coolant condition sensor is essentially a high impedance differential amplifier Q3' that receives the sense and reference potentials which have been level shifted by the PMOS transistors.

The level sensing portion comprises differential amplifiers Q4', Q5', and buffer Q6'. Capacitor C4' connected between pin VLVO and ground serves as a time delay to filter out any noise.

Resistor RH20 is connected between the supply voltage VCC and the positive input to amplifier Q4' while resistor RH21 is connected between that input and ground. Resistors RH22 and RH23 are respectively connected between the output of amplifier Q4' and its negative and positive inputs.

The output of amplifier Q4' is fed to the input of dual comparator Q5'. Diodes Q73 and Q74 are connected across the positive and negative inputs to comparator Q5' which in turn are connected through respective resistors RH24', RH25' to VCC and ground. Thus the diodes provide approximately a ±0.7 v comparator threshold range. That is, if there is a low level condition with the electrodes out of the liquid, amplifier Q4' begins to oscillate between ground and the positive supply rail. If there is any noise, the ±0.7 volts serves as a buffer so that the input to amplifier Q5' must go that much above or below in order to flip back and forth.

The output from amplifier Q5' is fed to hysteresis buffer Q6' which then is fed to a logic block composed of nor gates. The logic ensures that the corrosivity function is overridden by the level function so that a low coolant level condition takes precedence over the sensing of the corrosion inhibition characteristic of the coolant.

The output drive block indicated by dashed lines provides high current switching on the order of tens of milliamps. The buffers shown in effect represent two switches to ground. With a low level condition the two shut off so that VOUT pulls to VCC. When a corrosive condition occurs, the upper switch turns on which pulls the output to ground. During a normal condition the lower switch turns on to ground resulting in a voltage divider comprising R7' and R8' and giving half of the value of VCC.

With particular reference to FIG. 10 showing schematically the '81 device, the dashed line section CCS (coolant condition sensor) BIAS identified as A, comprises transistors Q70-72 and Q56-63 which serve as current sources to insure proper circuit bias in several device transistors.

Dashed line (Section B) comprises the Coolant Condition Comparator (Q3' of FIG. 8). The inputs VCRI− and VCRI+ are outputs from the '80 device. Transistors Q1-5 form a standard differential amplifier whose output feeds both the CCS Hysteresis (Section C) as well as the Output Logic (Section E). Current sources, transistors Q54, Q55 of the Bandgap Reference (Section D) connected as current mirrors supply bias current to the bases of transistors Q1 and Q2. The current sourced by transistors Q54 and Q55 whose bases are connected to the collector of transistor Q6 is determined by the resistor value connected to the BIAS pin 3 which is in series with emitter of transistor Q6.

Current supplied by transistor Q55 is also injected across the threshold resistor $R_{TH}$. The resulting voltage drop across this resistor determines the comparator threshold voltage. A potential at the VCRI+ input there is greater than the voltage drop across resistor $R_{TH}$ will turn off transistor Q5. This turns on transistor Q31 in the Output Logic (Section E) which allows current to bias transistors Q37 and Q38 on. A potential below the threshold value results in turning on transistor Q32 which in turn sinks bias current away from Q37. This results in shutting off Q37 which turns off output transistor Q38. Due to the external resistors R7', R8' (see FIG. 8) connected to VOUT1/VOUT and VOUT2 a corrosive indication results in a VOUT below 1 volt, a non-corrosive indication of approximately 2.5 volts and a low level indication above 4 volts. The output of the comparator section also feeds into the CCS Hysteresis (Section C).

The CCS Hysteresis (Section C) provides an adjustable amount of hysteresis for the coolant condition comparator and comprises transistors Q49–50, 64 and 65 and diode Q51. Input pins HYSI, HYSX and BIAS are used to set up the integrated circuit for either of two modes: internal or external hysteresis. The internal mode uses a connection between HYSI and BIAS. During a corrosive condition transistor Q5 is off which results in transistor Q49 turning on and Q50 off. Transistor 25 Q71 can then push bias current through diode Q51 which in turn flows through pin HYSI and through the $R_{BIAS}$ resistor connected to ground at the BIAS pin. A decrease in the current through transistor Q6 occurs which in turn decreases the current flow through 30 transistors Q54 and Q55. This results in a decreased voltage drop across the threshold resistor $R_{TH}$.

A noncorrosive condition causes transistor Q5 to turn on resulting in no current flow through Q51. This increases current through transistors Q6, Q54, and Q55.

The HYSX pin is used for external hysteresis. A resistor connected between pins HYSX and BIAS allows an adjustable hysteresis value. The current flow or absence of flow through Q65, R18 and the external resistors sets the hysteresis thresholds. Transistor Q64 biases the emitter of transistor Q65 at VCC/2.

The Bandgap Reference Section D of the circuit provides a well regulated reference which is utilized by other portions of the circuit and comprises transistors Q7–Q11 and Q58–Q63. A nominal 1.235 volt reference is supplied at the emitter of transistor Q6 ($R_{BIAS}$ pin). Resistor Q15 matches resistor $R_{BIAS}$ while transistor Q6 and Q7 VBE's are also matched. Transistors Q52 and Q53 are current mirrors used to minimize the bias current offset errors for transistors Q6, Q54 and Q55. Diode Q12 and Q13 are used in conjunction with transistor Q69 and Q66 to provide a two VBE potential allowing the bandgap to power up properly on application of power to the circuit. The current flow through Q54 and Q55 is a function of the bandgap voltage divided by the resistance at the BIAS or HYSX pins.

The Output Logic (Section E) uses inputs from the Coolant Level Buffer With Hysteresis (Section I) and the Coolant Condition Comparator (Section B) portions of the circuit. These inputs cause the Output Logic Circuit, (Sections F and J) to properly drive the output driver circuit to provide the appropriate output to the analog instrumentation input. The logic is configured to allow a low level indication to override both a noncorrosive and a corrosive indication. A corrosive coolant results in transistors Q5 being off, Q31, on and Q32 off.

This in turn allows Q70 current to bias transistors Q37 and Q38 on. With the resistor configuration on the output as described supra, this results in a sensor VOUT of less than one volt.

A noncorrosive condition causes transistor Q5 to turn on, transistor Q31 turns off and Q32 turns on, and bias current is taken away from the Driver #1 (Section F). Transistor Q34 turns off in addition to Q31, therefore providing bias current to Driver #2 (Section J). The resulting indication is one half of VCC. If there is a low level condition, transistor Q48 turns off which results in a turn on of both Q35 an Q33. This results in a turn off of Output Drivers #1 and #2 and a VOUT indication above 4 volts (assuming a 5 volt power supply).

The output pin VOUT1 of Driver #1 (Section F) is connected to two resistors (see FIG. 8), one to VCC, R8' and the other to R7'. The other end of R7' is connected to VOUT2. Pin VOUT1 is tied directly to the output VOUT. Resistors RH32 and RH34 are bias resistors and RE35 provides short circuit protection. Transistor Q36 turns on if the drop across resistor RE35 is above the transistor VBE. The turning on of Q36 limits the output current and protects Q38 from an overload condition.

The output in VOUT2 of Driver #2 (Section J) is connected to resistor R7' (FIG. 8) which is in turn is connected to input VOUT1. Resistors RH33 and RH36 are bias resistors and RE37 provides short circuit protection with transistor Q39 functioning in a manner similar to transistor Q36 of Section F.

The coolant level OP-AMP (Section G) comprises an input stage composed of transistors Q14–Q20, Q79 and Q80. Transistor Q69 is a current source used to provide a proper bias at the VLV+ pin input through resistors RH20 and RH21. Resistors RH22 and RH23 go from the output of the OP-AMP back to the inputs setting up the unstable oscillator front end. Capacitor C2 serves to improve the stability of the OP-AMP.

The resistor and capacitor R1'/C3' connected to the VLV− input (FIG. 8) form one leg of the unstable oscillator input. If the impedance of the other leg is greater, the OP-AMP breaks into oscillation. Otherwise a steady state output voltage results.

The output of the OP-AMP feeds directly into the inputs of two differential input pairs Q22, Q23 of the coolant level comparator (Section H). The remaining two inputs are taken from the resistor/diode divider leg formed by RH24, Q73, Q74 and RH25. This leg provides the threshold for these two differential amplifiers (in this case acting as comparators).

With no coolant level OP-AMP oscillation Q28 is turned off which results in a discharged capacitor which is connected to the VLVO pin. Oscillation causes Q28 to turn on which results in a charged capacitor and a turning off of transistor Q48.

During an adequate coolant level condition transistor Q28 is off and Q43 is on and Q47, Q46 and Q78 of Coolant Level Buffer with Hysteresis (Section I) are all turned on. Q67 and Q68 provide two VBE hysteresis with Q67/Q68 turning on or off dependent upon the state of the coolant level comparator. The capacitor provides a filtering time constant for the signal from the comparator. When transistor Q43 is turned on, Q48 is on and when Q43 is off so is Q48.

Figure 11:
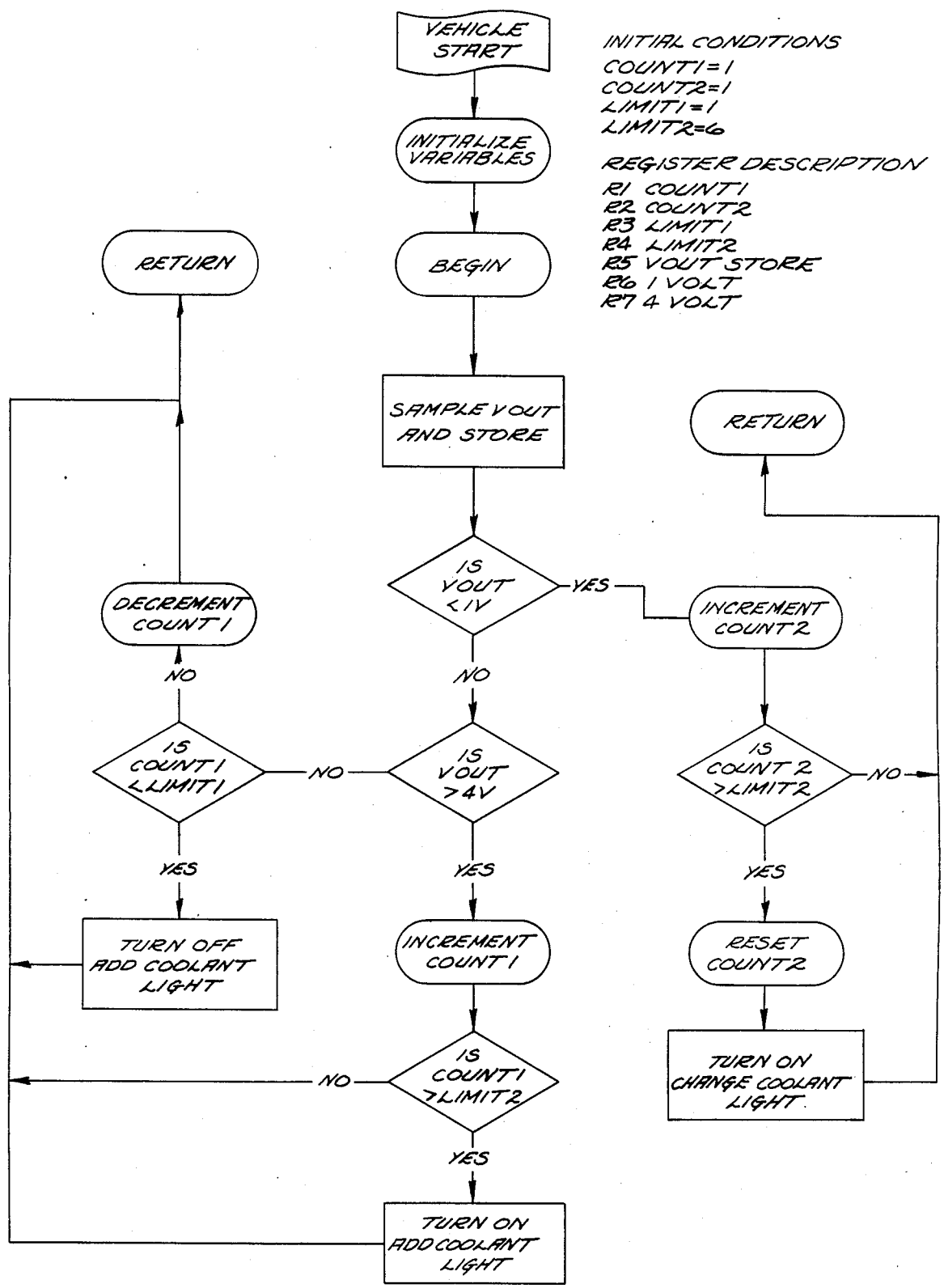
FIG. 11 is a flowchart showing an algorithm which can be used in controlling the energization of the warning lights indicating a low coolant liquid level and a failure of corrosion inhibition.

FIG. 11 shows a flowchart of an algorithm which can be used in conjunction with the engine control module (ECM) shown in dashed lines in FIG. 8 to obtain the desired performance including early warning to the driver of the vehicle of a low coolant condition which can lead to engine overheating and damage as well as early warning of a corrosive coolant condition which can lead to engine or cooling system failure. A selected number of samples, e.g. six, of low level indications will turn on an "add coolant" light in the dashboard of the vehicle (not shown). The light is turned off by a selected number of samples, e.g. six, of a normal coolant condition. The "change coolant" light (not shown) is turned on after a selected number of corrosive coolant samples (e.g. six). This light remains on for the remainder of the driving cycle, regardless of the add coolant indication.

Electrical performance characteristics of a system built in accordance with the invention are shown in Table I as follows:

TABLE I

| CHARACTERISTICS | MIN | TYPICAL | MAX | UNIT |
|---|---|---|---|---|
| Supply Voltage (VCC) | | 5.0 | | VOLTS |
| Supply Current (ICC) | | | 5 | MA |
| Corrosivity Threshold (V CAL) | 200 | | 400 | MV |
| Level Threshold (R LEV) | 0.5 | | 10.0 | K OHMS |
| "Corrosive" Output (VOUT) | | | 1.0 | VDC |
| "Noncorrosive" Output (VOUT) | 2.0 | 2.5 | 3.0 | VDC |
| "Low Level" Output (VOUT) | 4.0 | | | VDC |
| Operating Temperature Range | −40 | | +125 | DEG C |

This system incorporated components shown in Table II as follows:

TABLE II

| IC SN 28880 | (14 pin) |
|---|---|
| IC SN 28881 | (8 pin) |
| C1', C4', C5' | .1 µf monolithic ceramic chip capacitor |
| C3' | .0047 µf monolithic ceramic chip capacitor |
| C2' | .01 µf monolithic ceramic chip capacitor |
| R7' | 300 ohm thick film chip resistor |
| R8' | 348 ohm thick film chip resistor |
| R1' | 1.0K ohm thick film chip resistor |
| $R_{TH}$, $R_{DN}$ | select resistor - |
| PCB 32 | printed circuit board |
| $R_{BIAS}$ | 6.1K ohm thick film chip resistor |

Sensor systems made in accordance with the invention can of course be employed with liquids other than automotive coolants such as heat transfer liquids used in connection with energy systems or machine tools or the like.

In the foregoing specification, the invention has been described with reference to a specific exemplary embodiment thereof. However, it will be evident that various modifications and changes may be made thereunto without departing from the scope of the invention as set forth in the appended claims. The specification and drawings are accordingly, to be regarded in an illustrative rather than in a restrictive sense.

What is claimed is:

1. A liquid condition sensing system having electrode means adapted to be immersed in the liquid to sense electrochemical potentials including positive power supply means and a ground connection, voltage responsive means for providing an output dependent on the sensed electrochemical potentials, the output coupled to indication means to provide indication of selected first conditions of the liquid characterized in that potential level shifting means comprising CMOS devices are coupled to the power supply means and the ground connection, the CMOS devices having high input impedance and low leakage being coupled between the electrode means and the voltage responsive means so that potentials sensed by the electrode means are isolated from each other and ground and such potentials, which may include values within a selected range below ground, are shifted to positive potentials for input to the voltage responsive means; unstable voltage responsive means comprising bipolar devices having first and second inputs and an output are coupled between the electrode means and the indication means, one input to the unstable voltage responsive means serving as a reference and the second input to the unstable voltage responsive means coupled to the electrode means to sense a second condition of the liquid; and hysteresis means are coupled to the unstable voltage responsive means, the hysteresis means comprising a dual comparator coupled to the unstable voltage responsive means and a pair of diodes coupled between a plus and a minus input to the comparator.

2. A liquid condition sensing system according to claim 1 further characterized in that the potential level shifting means include two PMOS transistors, the electrode means comprising a reference electrode and a sensing electrode, the electrodes being coupled to respective gates of the two transistors.

3. A liquid condition sensing system according to claim 1 further characterized in that a selected level of impedance is coupled to an input of the voltage responsive means to provide a desired threshold level of the first condition for actuating the indication means.

4. A liquid condition sensing system according to claim 3 further characterized in that means are provided to adjust the threshold level of the voltage responsive means.

5. A liquid condition sensing system according to claim 1 further characterized in that a capacitive filter is coupled to the comparator to provide a selected time delay.

6. A liquid condition sensing system having electrode means adapted to be immersed in the liquid to sense electrochemical potentials including positive power supply means and a ground connection, voltage responsive means for providing an output dependent on the sensed electrochemical potentials, the output coupled to indication means to provide indication of selected first conditions of the liquid characterized in that potential level shifting means are coupled to the power supply means and the ground connection, the level shifting means having high input impedance and low leakage being coupled between the electrode means and the voltage responsive means so that potentials sensed by the electrode means are isolated from each other and ground and such potentials, which may include values within a selected range below ground, are shifted to positive potentials for input to the voltage responsive means; unstable voltage responsive means having first and second inputs and an output are coupled between the electrode means and the indication means, the first input to the unstable voltage responsive means serving as a reference and the second input to the unstable voltage responsive means coupled to the electrode means to sense a second condition of the liquid; and logic means are disposed between the outputs of the voltage responsive means and the unstable voltage responsive means and the input to the indication means, the logic means giving precedence to one of the first and second conditions in actuating the indication means, the logic means including first and second nor gates, the selected first conditions being an indication of corrosiveness of the liquid and the selected second conditioins being an indication of low liquid level and the second conditions taking precedence over the first conditions.

7. A liquid condition sensing system according to claim 6 further characterized in that the potential level shifting means include two PMOS transistors, the electrode means comprising a reference electrode and a sensing electrode, the electrodes being coupled to respective gates of the two transistors.

8. A liquid condition sensing system according to claim 6 further characterized in that a selected level of impedance is coupled to an input of the voltage responsive means to provide a desired threshold level of the first condition for actuating the indication means.

9. A liquid condition sensing system according to claim 8 further characterized in that means are provided to adjust the threshold level of the voltage responsive means.

10. A liquid condition sensing system according to claim 6 further characterized in that the electrode means includes a reference electrode of silver and a sensing electrode of two layered material comprising aluminum and steel.

11. A liquid condition sensing system according to claim 10 further characterized in that an output to the indication means of corrosiveness is approximately 1.0 volts, of noncorrosiveness between approximately 2.0–3.0 volts and of low level at least approximately 4.0 volts.

12. A liquid condition sensing system comprising electrode means having a reference electrode and a sensing electrode adapted to be immersed in liquid to sense electrochemical potentials, voltage responsive means coupled to the electrode means for providing an output dependent on the sensed electrochemical potentials, the output coupled to indication means to provide an indication of selected first conditions of the liquid, a CMOS integrated circuit and a bipolar integrated circuit, the CMOS integrated circuit having first and second PMOS transistors, each transistor having a gate, a source and a drain, the gate of each transistor connected to a respective electrode and the source of each transistor connected to the bipolar integrated circuit, the bipolar integrated circuit including the voltage responsive means, the potentials sensed by the electrode means being level shifted from levels which may include values within a selected range below ground to positive potentials within the common mode range of the bipolar integrated circuit.

13. A liquid condition sensing system according to claim 12 further comprising unstable voltage responsive means having first and second inputs and an output coupled between the electrode means and the indication means, one input to the unstable voltage responsive means serving as a reference and the second input to the unstable voltage responsive means coupled to the electrode means to sense a second condition of the liquid.

14. A liquid condition sensing system according to claim 13 further comprising logic means disposed between the outputs of the voltage responsive means and the unstable voltage responsive means and the input to the indication means, the logic giving precedence to one of the first and second conditions in actuating the indication means.

15. A liquid condition sensing system according to claim 14 further comprising a selected level of impedance coupled to an input of the voltage responsive means to provide a desired threshold level of the first conditions for actuating the indication means.

16. A liquid condition sensing system according to claim 15 further comprising means to adjust the threshold level of the voltage responsive means.

17. A liquid condition sensing system according to claim 13 further characterized in that the unstable voltage responsive means are bipolar devices.

18. A liquid condition sensing system according to claim 17 further characterized in that hysteresis means are coupled to the unstable voltage responsive means.

19. A liquid condition sensing system according to claim 18 further characterized in that the hysteresis means includes a dual comparator having three inputs, the output of the unstable voltage responsive means connected to one input of the comparator, and a pair of diodes connected across the other two inputs of the comparator to provide 2 VBE potential hysteresis.

20. A liquid condition sensing system according to claim 19 further characterized in that the hysteresis means includes a variable time delay network having a discrete comparator coupled between the output of the unstable voltage means and ground to filter out low level noise.

21. A liquid condition sensing system according to claim 18 further characterized in that the hysteresis means includes a variable time delay network having a discrete comparator coupled between the output of the unstable voltage means and ground to filter out low level noise.

* * * * *